United States Patent [19]

Reller et al.

[11] Patent Number: 5,002,527
[45] Date of Patent: Mar. 26, 1991

[54] TRANSDERMAL DRUG DELIVERY APPLICATORS

[75] Inventors: Chana Reller, Petach Tikva; Joseph Gross, Moshav Mazor. both of Israel

[73] Assignee: Inventor's Funding Corp. Ltd., Tel-Aviv, Israel

[21] Appl. No.: 280,500

[22] Filed: Dec. 6, 1988

[51] Int. Cl.⁵ .................................................. A61N 1/30
[52] U.S. Cl. .......................................... 604/20; 128/798
[58] Field of Search .......................... 604/20, 284, 304; 128/303.13, 419 R, 421, 635, 639, 783, 644, 798, 799, 802, 803

[56] References Cited

U.S. PATENT DOCUMENTS

| | | | |
|---|---|---|---|
| 3,677,268 | 7/1972 | Reeves | 604/20 |
| 4,177,817 | 12/1979 | Bevilacqua | 128/802 |
| 4,211,222 | 7/1980 | Tapper | 604/20 |
| 4,325,367 | 4/1982 | Tapper | 604/20 |
| 4,416,274 | 11/1983 | Jacobsen et al. | 604/20 |
| 4,419,091 | 12/1983 | Behl et al. | 604/20 |
| 4,474,570 | 10/1984 | Ariura et al. | 604/20 |
| 4,474,570 | 10/1984 | Ariura et al. | 604/20 |
| 4,640,689 | 2/1987 | Sibalis | 604/20 |
| 4,658,819 | 4/1987 | Harris et al. | 128/303.13 |
| 4,708,716 | 11/1987 | Sibalis | 604/20 |
| 4,722,726 | 2/1988 | Sanderson et al. | 604/20 |
| 4,725,263 | 2/1988 | McNichols | 604/20 |
| 4,725,263 | 2/1988 | McNichols | 604/20 |
| 4,731,926 | 3/1988 | Sibalis | 602/20 |
| 4,809,707 | 3/1989 | Kraft | 604/20 |
| 4,820,263 | 4/1989 | Spevak et al. | 128/798 |
| 4,883,457 | 11/1989 | Sibalis | 604/20 |

FOREIGN PATENT DOCUMENTS

| | | | |
|---|---|---|---|
| 8607269 | 12/1986 | PCT Int'l Appl. | 128/419 |
| 8808729 | 11/1988 | PCT Int'l Appl. | 604/20 |
| 2041752 | 9/1980 | United Kingdom | 604/20 |

Primary Examiner—John D. Yasko
Assistant Examiner—A. Gutowski
Attorney, Agent, or Firm—Charles E. Baxley

[57] ABSTRACT

An iontophoretic device is taught which is positionable on skin of a recipient. An insulating member includes therethrough at least one reservoir containing a drug between outer and inner (recipientwise) electrodes adhered to surfaces of the insulating member. The inner electrode preferably is spaced from a rim of the drug reservoir by the same distance as the depth and width of the reservoir. The electrodes are connected to field generating means which draw the ionic drug into the patient and outward from the rim of the reservoir.

6 Claims, 4 Drawing Sheets

TRANSDERMAL DRUG DELIVERY APPLICATORS

BACKGROUND OF THE INVENTION

The present invention relates to a device for delivery of charged drug molecules through the skin, employing an iontophoresis phenomena.

Recently, iontophoresis has gained increased attention as an effective method for topical application of ionic agents or drugs by promoting absorption through skin of a human or animal. Iontophoresis techniques are disclosed in, for example, Glass JM et al., Int. J. Dermatol. 19,519 (1980); Russo, J., A., J. Hosp. Pharm. 37,843 (1980); Gangarosa LP et al., J. Pharmacol. Exp. Ther. 212,377 (1980); Hill JM et al., Ann. NY. Acad. Sci. 284,604 (1977).

Iontophoresis has been used for transdermal delivery of charged molecule drugs into the skin. The method employs a dc voltage between two electrodes, attached to the skin, and under one of said electrodes there is provided a layer of the drug to be introduced. The drug is migrated into the skin due to the applied electric field.

Because of impedance of the outer layers of the skin, the drug penetrates the body's interstitial fluids, from which it is diffused into the body.

These electric fields contain a large amount of ions, by which electric current is passed into the body. A main disadvantage found in iontophoresis is the fact that it causes burns and irritation to the skin. This effect can be explained by the high impedance between the two electrodes which results in the development of a very high power converted into heat thusly causing skin burns. In order to eliminate these skin burns the impedance between the two electrodes must be decreased.

In an equivalent circuit to that described above (such as the human membrane) Pilla et al describe in the Journal of Electro Chemical Society 124 (1977) 1697, a circuit containing capacitors and resistors. Thus they concluded that in order to increase migration current, the impedance of the capacitors and resistors should be decreased.

The impedance of a capacitor is inversely proportional to the frequency. Increasing the frequency decreases the impedance of the capacitor and decreases the impedance of the human body.

Experiments showed that applying square wave pulses of 0 volts to 4 volts and a duty cycle of 1:1 at 50-500 kHz, and having a peak current of 50 mA, with an average current of 12 mA, passed through the human body, without causing burns. The foregoing suggest that application of pulses at a current or voltage of various shapes, at high frequency will accomplish the desired objective.

Another way to reduce the body's impedance is to decrease the ohmic resistance. The ohmic resistance between two electrodes depends on the configuration of the electrical cell. In a planar configuration, which consists of two planar parallel electrodes, the resistance depends on the gap between the electrodes. By decreasing the gap the electrical field increases, causing a decrease in resistance.

In a concentric cylinder configuration, most of the ohmic potential drop occurs near the inner cylinder and does not depend solely on the electrode gap. In a circular planar electrode, most of the ohmic potential drop occurs at a region of the same order of magnitude as the radius of the electrode, and is proportional to the radius.

By changing the configuration of the electrodes, the ohmic resistance can be changed too, this is shown by J. Newman et al. in Electrochemical Systems, published by Prentice-Hall, Englewood Cliffs, N.J. (1973).

There is no convenient way to produce planar or cylindrical configurations, using the human body as the electrical medium. The circular planar electrode is more convenient. However, it was shown by Aoki et al. "Electro Chemical Journal" that thin longitudinal electrodes resemble the behavior of cylinders. This fact also enables use of thin rectangular electrodes.

A strong effect of cell configuration on iR (current x resistance) drop was shown by Bond et al, Electronal Chem. (1984) 257. They were able to take electrochemical measurements of extremely non conductive electrolytes, at temperatures down to the freezing point of the solvent (eutectric mixtures)—solvents such as acentonitrile and acetone—by using small circular electrodes.

At these low temperatures measurements large electrodes cannot be utilized because ohmic resistance is very high.

The electrolyte is non-uniform and may contain even insulating regions. Even though the human body is non-uniform and has high specific resistance, the effect of size and shape of the electrodes influences the resistance between the electrodes.

Other structures and designs of iontophoretic transdermal devices were described in the following patents:

1. United Kingdom Patent GB2104388 describing a light device consisting essentially of two electrodes, a current being conducted between these electrodes through a patient's body, causing an ionized drug to be forced through the skin.
2. U.S. Pat. No. 4,141,359 describes an iontophoresis device, having means for predetermined settings of limits of impedance enabling control of currents, hence control of drug flow.
3. U.S. Pat. No. 4,164,226 describes inhibition of perspiration, although it also maintains general iontophoretic applications. Burns on the skin are eliminated by interposing a relatively thick porous and preferably moistened material between a negative electrode and the skin. Electrodes with separate conductive areas are suggested.
4. U.S. Pat. No. 4,419,092 describes a structure of an electrode for use in electrophoretic devices having a membrane through which ions can migrate into skin, and include an electrode mounted on top of a reservoir connected to an energy source.
5. U.S. Pat. Nos. 4,557,724 and 4,640,689 as its continuation in part describe systems whereby drugs are charged electrically in a reservoir and driven towards the skin into the blood stream by passing a current through the skin between two electrodes which are connected to a power source.
6. U.S. Pat. No. 4,764,164 describes a device for iontophoresis which includes a pulse generator, a working electrode and a counter electrode. The device has means for discharging and charging the charges accumulated in the electrodes during intermission periods between the pulses generated by the pulse generator. The device claims to eliminate the irritation and burns of the skin. The effective operation time of the device is 20% of the total time applied at relatively high currents of 10-30 mA. The major feature of said patent is reduction of skin capacitor impedance by using a high frequency pulse.

The iontophoretic device disclosed in prior art known to us generally include connecting an output terminal of a continuous direct current generator or pulse generator to a working electrode composed of a metal plate or other conductive substances. These last mentioned electrodes are covered with a gel, or a moistened pad of porous material impregnated with an aqueous solution, including an ionic drug and a counter electrode structured similar to the working electrode but without the drug.

From the foregoing description, is should be clear that the actual application of iontophoresis through these prior art techniques has major disadvantages including but not limited to low efficiency and skin burns. Although iontophoresis is a very effective method for drug application, these disadvantages have limited its widespread use.

By way of explanation, in all of these foregoing iontophoresis approaches the following major problems recur.

1. Because of the high impedance of a human or animal body, an application of electric current causes a larger power to develop which converts into heat with resultant burns and irritation to the skin of the recipient using the device.
2. Electrode designs in devices described in the prior art known to us do not teach specific geometric relations to solve this burn problem by reduction of ohmic resistance of the skin. This inadequacy is overcome by the devices which are the subject of this invention.

Accordingly, it is an object of the present invention to eliminate the above mentioned problems in the prior art by providing an iontophoretic device capable of sufficiently decreasing the skin's total impedance (ohmic resistance and capacitor impedance) thereby allowing an iontophoretic device to be used under a relatively low voltage and a relatively high electric current, also permitting the iontophoretic device to be applied safely to the human or animal skin under a high current without causing irritation, burns and rubefaction of the skin.

Another object of the present invention is to provide an iontophoretic device which is light in weight, easily manufactured and assembled and capable of direct and simple application to a recipient's skin and which can be operated over a long period of time.

DESCRIPTION OF THE INVENTION

Figure 1:
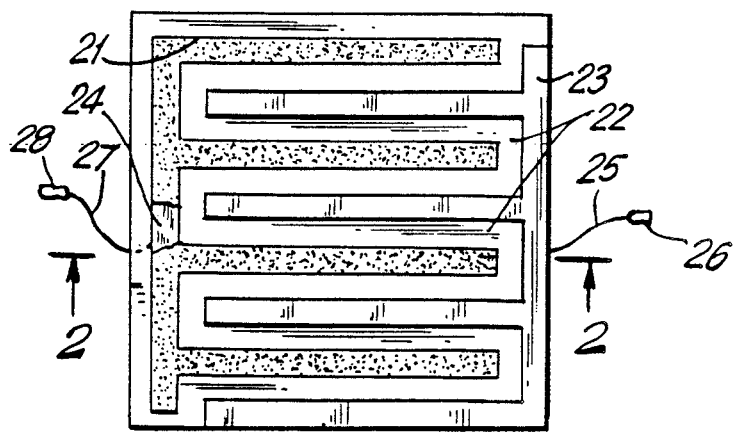
FIG. 1 is a schematic plan view of an embodiment of the invention in the form of a patch and having fork like grooves as drug reservoirs, and also shows complementary multi electrodes.
Figure 2:
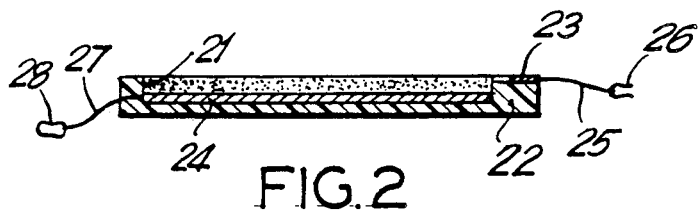
FIG. 2 is a schematic end view of the patch shown in FIG. 1.

An iontophoretic device according to the present invention comprises a supporting member including means for attaching same to a human or animal recipient who is to receive a drug. The iontophoretic device is covered by a release protecting foil on its side to be attached to the recipient's skin. Connected to the supporting member is a continuous thin conductive sheet adhered to an insulating layer having cavities going through the insulating layer preferably at various locations. There are polar solutions or gels of ionic drugs introduced into the cavities. On an inner surface of the insulating layer is a thin preferably continuous conductive sheet forming an electrode connectable to an electrical power supply preferably consisting of a power source, optionally having a pulse generator, and a current control means all operatively connected to said multi electrodes by two connectors so that when the electric power source is switched on the pulsing generator supplies pulses of high frequency, waveforms in a desired duty cycle, under voltage from the power source. The current causes migration of the polar ions of the drug being applied into the recipient through its skin. The combination of the high frequency of the pulse and the specific electrode system of this invention reduces the body impedance and increases the current migration at relatively low voltages. This electrode form and mode of operation increase the device's efficiency without causing undesirable irritation or burns to the human skin.

In one embodiment of the invention the electrodes are in a form of continuous thin conductive layers adhered to an insulating plate having fork shaped grooves filled with a gel or a cellular sponge absorbing material containing the drug in solution. There is also provided a thin conductive layer in the form of a complementary fork to said grooves and intermeshed between the grooves. To achieve high efficiency of the device the width of the grooves, and the width of the conductive layer and the distance between the layer and the groove or grooves should all be equal in size to the depth of the cellular sponge layer or gel containing the drug.

In another and most preferred embodiment of the invention the electrodes are in the form of a continuous thin conductive layer connected to an insulating layer which has punched circular holes through it. The holes are filled with a gel or a cellular sponge absorbing material containing the drug solution. This embodiment includes also a complementary circular thin conductive layer connected on top of said insulating layer. Said circular layer being larger in size than the punched holes. To achieve efficiency of the device the depth and diameter of the said cellular sponge material or gel containing the drug, in the formed or punched hole, preferably should be equal to the radius differential of the punched thin top conductive layer, and the radius of the punched hole.

In another embodiment of the invention the electrode system is in the form of a series of concentric circular grooves going through said insulating layer containing the cellular absorbent material or gel with the drug and having complementary formed rings of a thin conductive layer. For efficiency of the device the width of the rings, the width of the grooves, and the distance between the rings and the grooves preferably should be equal or close in size to the depth of the cellular material or gel containing the drug.

In another embodiment of the invention the inner electrode is in the form of punched small squares in the insulating layer into which the cellular material or gel containing the drug is introduced. A thinly formed conductive layer connected to the inner surface of the iontophoresis member is in the form of complementary larger squares surrounding the punched squares. The best efficiency of the device will occur when the depth of the said cellular material or gel in the punched holes is similar in size to the size of the punched square and similar in size to the distance between the thin top conductive layer to the square, and the width of the conductive square grids.

In another embodiment of the invention the electrode system is in the form of a continuous snail like groove punched through the insulating layer and filled with said cellular material or gel containing the drug. The thin conductive layer is formed as a complement of the snail like groove and connected in the space between the grooves on top of the insulating layer. Efficiency is improved when the depth of the cellular material or gel is similar or equal to the groove width, the width of the inner electrode, and the distance between the rim of the groove and said electrode.

The electric power supply unit or field generating means may consist of a power source the form of a battery having a voltage of 3 to 9 volts. The battery can either be a dry-cell battery, a lithium battery or a rechargeable nickel-cadmium battery enabling the user to have a minimum of 8 to 10 hours use at a required current range of 5–50 mA. Optionally there can be a pulse generator preferably having a frequency range of 50–500 kHz and a switch mechanism placed in parallel between the electrodes. A microprocessor enables the user to establish a therapeutic program and is in series with the pulse generator.

In a further embodiment of the invention the drug reservoirs are arranged in one or more holes or grooves formed from the insulating layer and either filled with a drug containing gel or comprise a cellular or similar absorbent sponge material soaked with the drug solution. The reservoirs can be made of either cellulose, fiberous elastomeric or plastic foamed material. The insulating layer between the electrodes can be made of a pliable plastic or elastomeric insulator material acting also as a holder for the cellular sponge or material soaked with the drug or for said gel containing the drug. The thin conductive electrode sheets can be made of thin aluminum foil or any other suitable metal foil or of a thin carbon layer or carbon fiber non woven web or woven carbon fiber matting. The conductive electrodes can preferably be made of a suitable substrate coated with silver or another suitable conducting material preferably at a coating thickness in the order of 5M.

In another embodiment of the invention the power supply unit or field generating means is mounted on a separate member connected (for example) to the electrode and drug carrying member by two quick connectors, one to each of the electrodes (recipientwise inner cathode or outer anode). This embodiment enables use of the electrode and drug carrying member for a single treatment and for any required length of time or for any required specific drug. Once the treatment is completed or the drug in the reservoirs is exhausted the electrode member (with all the related components) can be disposed of and the power supply unit or field generating means can be disconnected and reused for a next treatment until the power source or battery is exhausted.

DESCRIPTION OF THE PREFERRED EMBODIMENTS

FIG. 1 illustrates a device according to the present invention and having a flat continuous recipientwise outer metal foil 24 adhered to the bottom (outer) side of an insulating member 22 having a groove 21 filled with a gel or a cellular absorbent material containing an ionic drug. The groove 21 is in the form of a fork in its plain view as shown in FIG. 1. An inner thin electrode 23 is formed as a mating fork to groove 21 to mate with tines of the groove 21 and is connected on the inner side of the insulating layer 22. The width of the groove 21 is equal or similar in size to the widths of the electrode 23 and the distance between the electrode 23 from the rim of the groove 21. Also the distance between the electrode 23 and the rim of the groove 21 should be equal or similar in size to the depth of the cellular layer sponge or gel which contains the drug. Leads 25 and 27 connect metal foils to connectors 26 and 28 which are connected to the power supply or field generating means (not shown).

Figure 3:
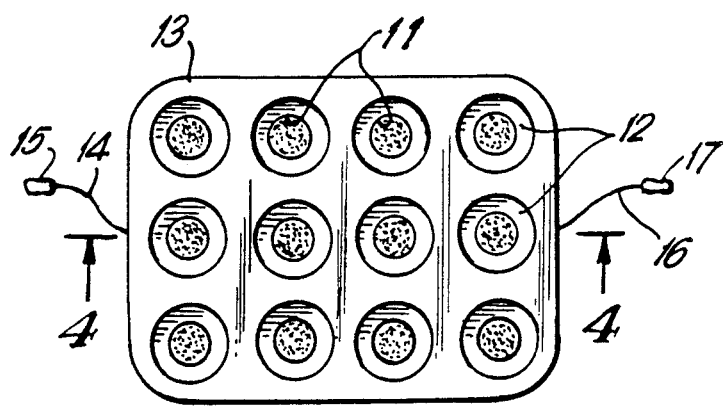
FIG. 3 is a plan view showing another and preferred embodiment of the invention including circular holes as the drug reservoirs, and a continuous inner electrode spaced from the holes.
Figure 4:
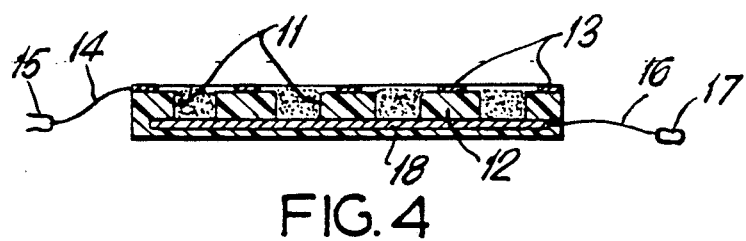
FIG. 4 is a cross sectional view taken on line 4—4 of FIG. 3.

FIG. 3 illustrates a preferred device according to the present invention having a continuous metal foil 18 (which may be aluminum or a silver coated substrate), an insulating layer 12, having punched holes 11 containing the drug in an absorbent cellular medium or a gel. A thin continuous inner metal foil 13 is connected on the inside (recipientwise) insulating layer 12. Wire leads 14 and 16 connect the metal foils 18 and 13 to a power supply unit or field generating means (not shown) by the two connectors 15 and 17 respectively. The depth of the holes 11 is of the same or similar size to the radius differential between the hole size, and foil as will be clear from FIG. 4.

Figure 5:
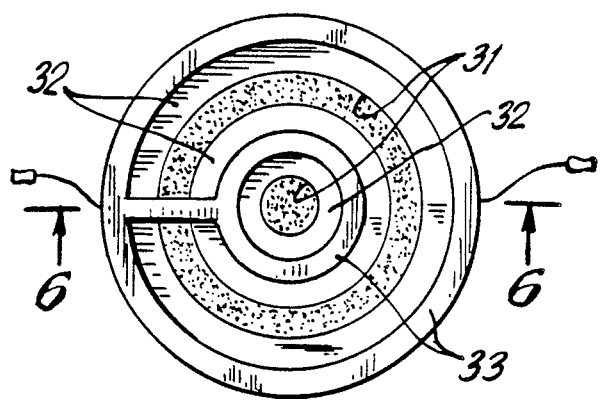
FIG. 5 is a plan view showing another embodiment having ring like grooves forming drug reservoirs with continuous inner ring like electrodes spaced from the grooves.
Figure 6:
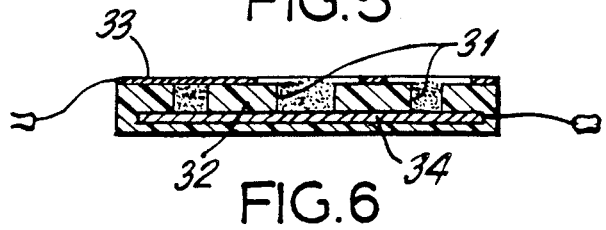
FIG. 6 is a cross sectional view taken on lines 6—6 of FIG. 5.

FIGS. 5 and 6 illustrate a device according to the present invention having a ring shaped electrode system. A metal foil 34 is connected to the outside of an insulation layer 32 having ring shaped grooves 31 filled with cellular absorbent material or gel containing a drug. A second metal member 33 also in the form of a ring is mounted on the inner surface of insulating layer 32 between the grooves 31. Thickness of the grooves is equal or similar in size to the distances between the insulation layer and grooves and also the distance between the inner electrode and the grooves.

Figure 7:
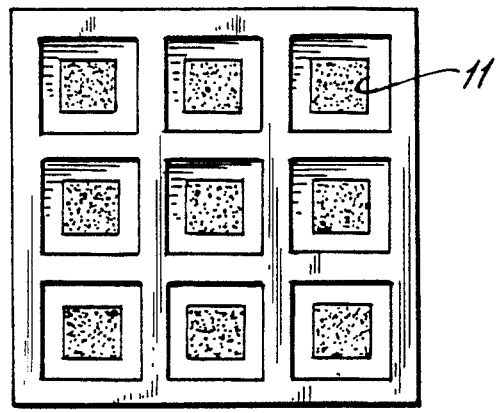
FIG. 7 is a plan view illustrating another embodiment of the invention having square grooves forming drug reservoirs, with a continuous inner electrode spaced from the holes.
Figure 8:
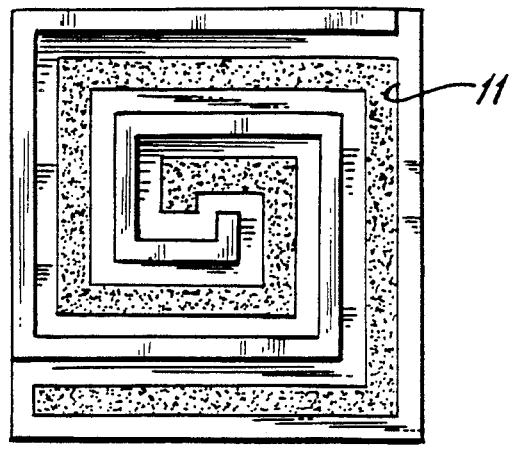
FIG. 8 is a plan view illustrating another embodiment having a snail like groove forming a drug reservoir, and a snail like inner electrode spaced from the groove.

FIG. 7 illustrates an electrode with square reservoirs in plan view. FIG. 8 illustrates an electrode with a snail like reservoir and complementing upper (inner) electrode). Referrring to FIGS. 7, 8 and 9, it should be noted that they show an embodiment of the present iontophoretic device as a block diagram for simplicity of illustration.

Figure 9:
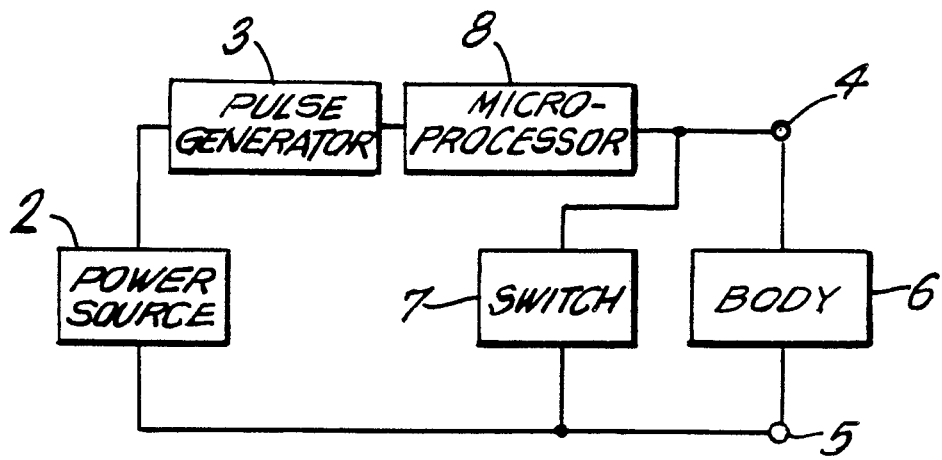
FIG. 9 illustrates schematically an electrical diagram of a preferred power supply unit.
Figure 10:
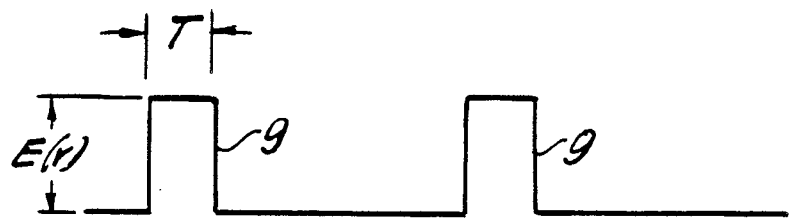
FIG. 10 illustrates schematically a preferred frequency wavelength sequence of the pulse generator.

FIG. 9 comprises a power source or field generating means 2 (e.g., a dry element battery having a voltage of 4 V), a pulse generator 3 capable of generating a voltage pulse having a frequency of 50–500 kHZ as shown in FIG. 10. A working electrode 4 containing an ionic agent, a counter electrode 5, a human or animal body designated 6 connected to the working and counter electrodes 4 and 5, and a switch mechanism 7. A microprocessor unit 8 is included for introducing a preset therapeutic program.

Figure 11:
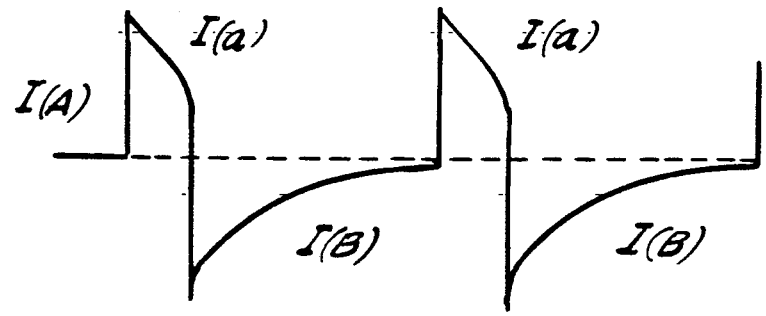
FIG. 11 is a graph of current entering the recipient's body.

The switch mechanism 7 is in parallel to the human or animal body 6, for depolarizing the potentials of the counter electrodes 4 and 5, preferably for bringing the polarized potentials of the electrodes 4 and 5 to an equal level simultaneously with stoppage of therapeutic pulses 9 generated from the pulse generator 3. That is, according to this mechanism, the residual charge (i.e. polarization) in the polarization capacity is discharged or depolarized by shortcircuiting the electrodes 4 and 5. When this field generating means is applied to the human or animal body 6, the current passing into the body is shown in FIG. 11. That is, during output time period T of the therapeutic pulse shown in FIG. 11, the current (i.e., pulse current Ia) flows mainly to the polarization impedance of the skin of the body 6, and the ionic agent contained in the working electrode 4 is mainly endermically absorbed. Stated differently, the field generating means draws the ionic drug into the patient and outward from the reservoir.

FIG. 12, 13, 14, 15 and 16 illustrate different views of a complete patch member before use and when applied to skin of a recipient.

Figure 12:
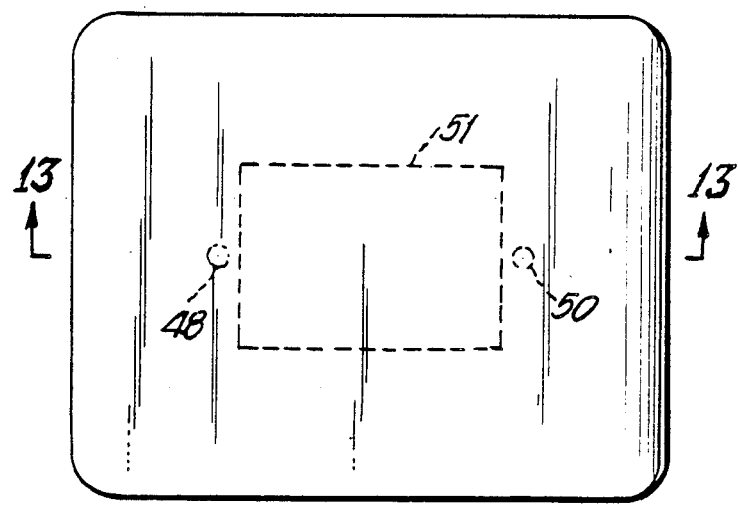
FIG. 12 shows a plan view of a patch according to this invention.

FIG. 12 shows a top view of a patch illustrating the member 45 connected to the recipient (not shown) and the power supply unit or field generating means 51 having two connectors 50 and 48 connecting unit 51 to member 45.

Figure 13:
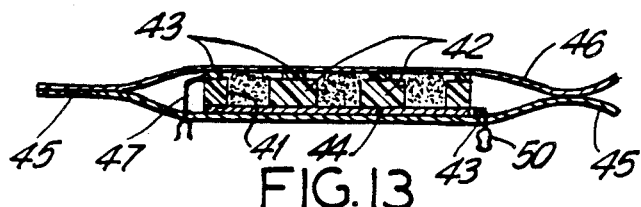
FIG. 13 is a cross sectional view of the patch member taken on line 13—13 of FIG. 12.

FIG. 13 is a cross sectional view of the device shown in FIG. 12. The member 45, carrying the unit which connects to the power supply member 51 by connectors 50 and 48, through leads 47 and 49 also is connected to both thin metal foils 43 and 44.

Figure 14:
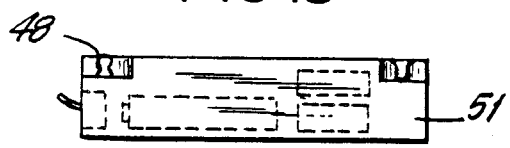
FIG. 14 is a cross sectional view of the power supply unit taken on line 14—14 of FIG. 15.
Figure 15:
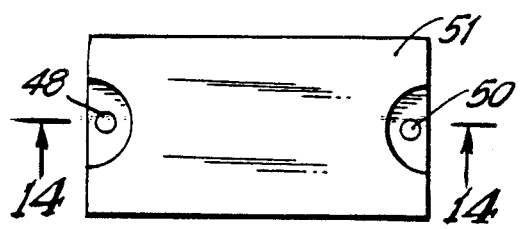
FIG. 15 is a plan view of the power supply unit.
Figure 16:
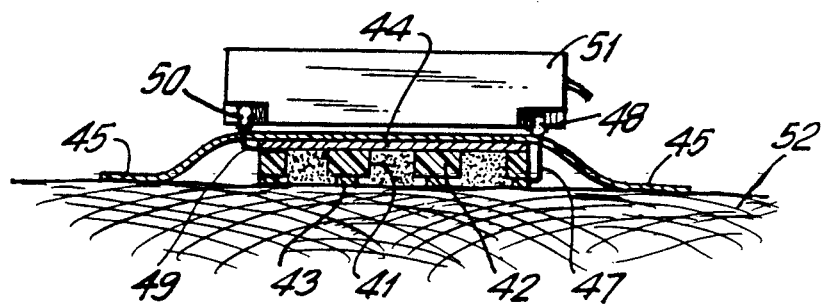
FIG. 16 is a cross sectional view of the patch with the power supply unit assembled therewith, and shown applied to a recipient's skin.

The insulating layer 42, and the drug reservoirs 41 are grooves in the insulating layer containing either cellular material soaked with the drug solution or a gel containing the drug. A protective detachable foil 46 optionally protects the device and the drug during shipping and storage. FIG. 14 and 15 illustrate the power supply unit or field generating means 51, with the two connectors 50 and 48. FIG. 16 illustrates the device when applied to human or animal skin 52 after removing a detachable foil 46.

The power supply unit or field generating means 51 is connected to the member 45 by connectors 50 and 48 through leads 47 and 49, which are connected to thin metal foil electrodes 43 and 44, respectively. The drug solution is stored in the grooves (or reservoirs) 41 either in cellular absorbing material, or in a gel. The member 45 is attached to the skin 52 of a recipient as by a suitable adhesive.

When the battery (not shown) is switched on and the pulsing generator starts to supply electric pulses at the required frequency, the current passes through one of the poles of the battery through the connector 50 to lead 49 into the outer foil electrode 44, then through the drug reservoirs 41 inward into the human or animal body, returning to the inner conductive foil electrode 43 thence through the lead 47 and connector 48 to the other pole of the battery. Thusly the current passing through the ionized drug solution in the reservoir, drawing the ions patientwise through the skin and outward of the reservoir into the body.

It should be understood that specific forms of the invention herein illustrated and described are intended to be representative only as certain changes may be made in the invention without departing from the teaching of this disclosure. Accordingly, references should be made to the following claims determining the full scope of this invention.

We claim:

1. An iontophoretic device comprising in combination:
    an insulator member having an inner surface adapted to be positionable in juxtaposed relationship to skin of a recipient; at least one reservoir formed in the insulating member and including an opening in the inner surface and containing an ionic drug and terminating in a rim formed at the opening in the inner surface;
    an outer electrode positioned outward from the inner surface and in contact with the drug;
    an inner electrode provided on the inner surface of the insulating member and spaced away from the rim of the reservoir;
    the rim of the reservoir and the inner electrode defining a gap therebetween;
    the electrodes being connectable to a field generating means for energizing the electrode to draw the drug from the outer electrode in the field toward the inner electrode into the skin of the recipient;
    the reservoir having a forked configuration; and
    the inner electrode having a forked configuration complementary to that of the reservoir.

2. The iontophoretic device in claim 1 with
    the reservoir having a predetermined depth measured from the outer electrode to the inner surface, and
    with the width of the gap substantially equal to the depth.

3. The iontophoretic devise of claim 1 with
    the insulating member comprising a flat plate having an outer surface, the reservoir passing completely through the insulating member from the outer surface to the inner surface,
    the outer electrode adhered to the outer surface, and
    the inner electrode adhered on the inner surface.

4. An iontophoretic device comprising in combination:
    an insulator member having an inner surface adapted to be positionable in juxtaposed relationship to skin of a recipient;
    at least one reservoir formed in the insulating member and including an opening in the inner surface and containing an ionic drug and terminating in a rim formed at the opening in the inner surface;
    an outer electrode positioned outward from the inner surface and in contact with the drug;

an inner electrode provided on the inner surface of the insulating member and spaced away from the rim of the reservoir;

the rim of the reservoir and the inner electrode defining a gap therebetween;

the electrodes being connectable to a field generating means for energizing the electrodes to draw the drug from the outer electrode in the field toward the inner electrode into the skin of the recipient;

both the reservoir and the inner electrode having mating outwardly spiralling configurations.

5. The iontophoretic device in claim 4 with the reservoir having a predetermined depth measured from the outer electrode to the inner surface, and with the width of the gap substantially equal to the depth.

6. The iontophoretic device of claim 4 with the insulating member comprising a flat plate having an outer surface, the reservoir passing completely through the insulating member from the outer surface to the inner surface, the outer electrode adhered to the outer surface, and the inner electrode adhered on the inner surface.

* * * * *